United States Patent
Maanum

[11] Patent Number: 5,360,390
[45] Date of Patent: Nov. 1, 1994

[54] PROSTHETIC DEVICE WITH A RETAINING STRAP

[76] Inventor: Armand D. Maanum, 2300 Douglas Dr. N., Golden Valley, Minn. 55422

[21] Appl. No.: 156,878

[22] Filed: Nov. 23, 1993

Related U.S. Application Data

[63] Continuation of Ser. No. 872,629, Apr. 22, 1992, abandoned, which is a continuation-in-part of Ser. No. 600,612, Oct. 19, 1990, abandoned.

[51] Int. Cl.$^5$ .............................................. A61F 5/00
[52] U.S. Cl. .................................................... 600/39
[58] Field of Search ................... 600/38, 39, 40, 41; 128/844; 604/349–353

[56] References Cited

U.S. PATENT DOCUMENTS

| | | | |
|---|---|---|---|
| 1,206,324 | 4/1916 | Hart | 128/79 |
| 1,362,398 | 12/1920 | Crawford et al. | 128/79 |
| 1,383,944 | 7/1921 | Hart | 128/79 |
| 1,585,861 | 5/1926 | Huff | 128/79 |
| 2,471,360 | 2/1947 | Thorne | 128/79 |
| 2,868,192 | 1/1959 | Dannen | 128/79 |
| 2,899,957 | 8/1959 | Briggs | 128/79 |
| 3,495,588 | 2/1970 | Walters | 128/79 |
| 3,648,700 | 3/1972 | Warner | 128/294 |
| 3,920,007 | 11/1975 | Line | 128/79 |
| 3,939,827 | 2/1976 | Brunsletter | 128/79 |
| 3,982,530 | 9/1976 | Storch | 128/79 |
| 4,074,712 | 2/1978 | Wright | 128/79 |
| 4,194,502 | 3/1980 | Eckels | 600/39 |
| 4,224,933 | 9/1980 | Reilling | 128/79 |
| 4,449,521 | 5/1984 | Panzer | 128/79 |
| 4,615,337 | 10/1986 | Allinson | 128/79 |
| 4,672,954 | 6/1987 | Panzer | 128/79 |
| 4,893,616 | 1/1990 | Immonen | 128/79 |
| 4,972,849 | 11/1990 | Park et al. | 128/79 |

OTHER PUBLICATIONS

Minneapolis Star Tribune article, Nov. 4, 1990 by Jane Brody.
Minneapolis Star Tribune article, Nov. 11, 1990 by Jane Brody.

*Primary Examiner*—David Isabella
*Assistant Examiner*—Debra S. Brittingham
*Attorney, Agent, or Firm*—Merchant, Gould, Smith, Edell, Welter & Schmidt

[57] ABSTRACT

A device is provided for use as a prosthesis in supporting the penis of a wearer, during intercourse. The prosthesis comprises an elongate trough member and an arrangement for maintaining the trough member in operative association over the user's penis, during performance of intercourse. In certain embodiments a retaining strap provided to facilitate retaining of the prosthesis in place.

2 Claims, 5 Drawing Sheets

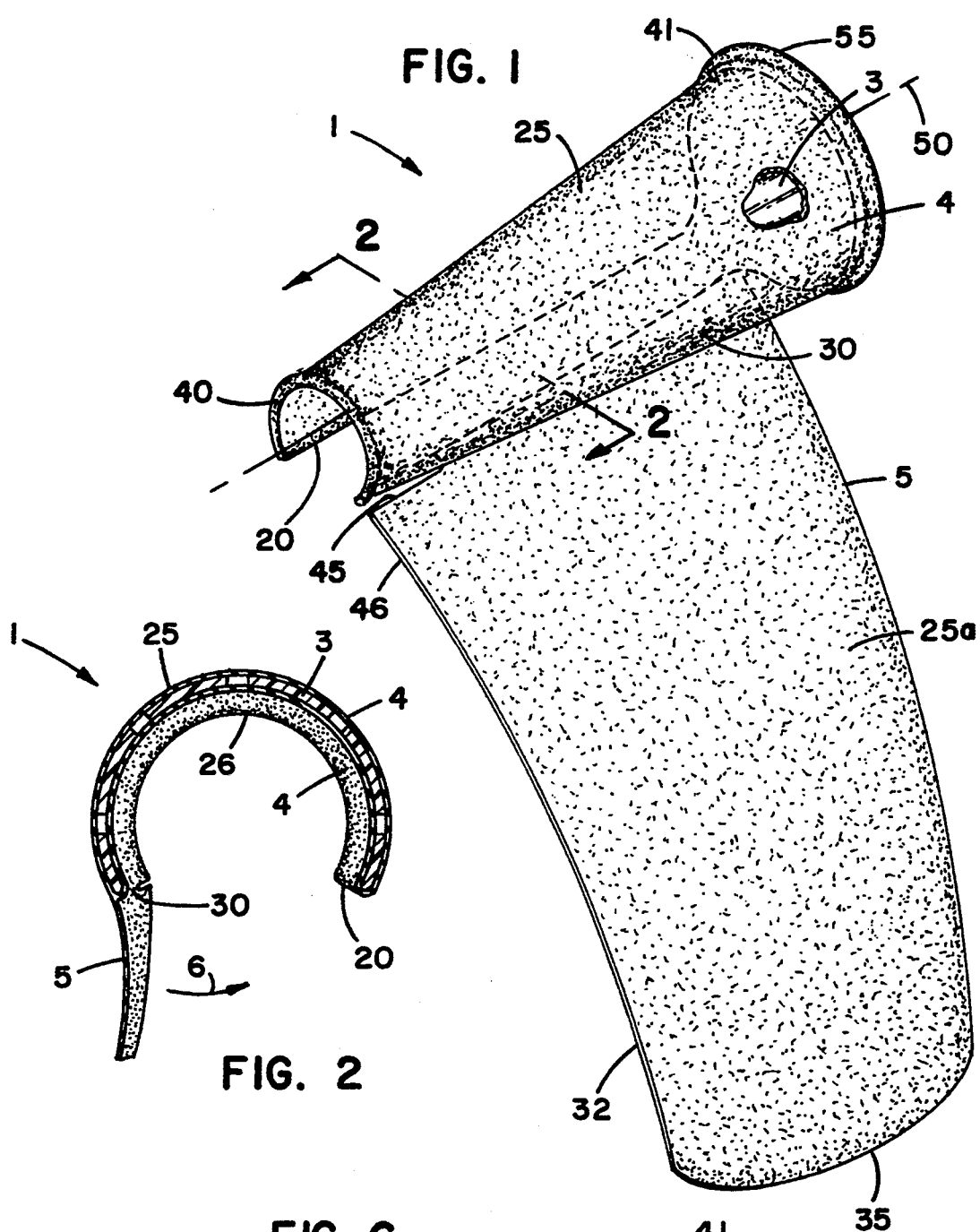
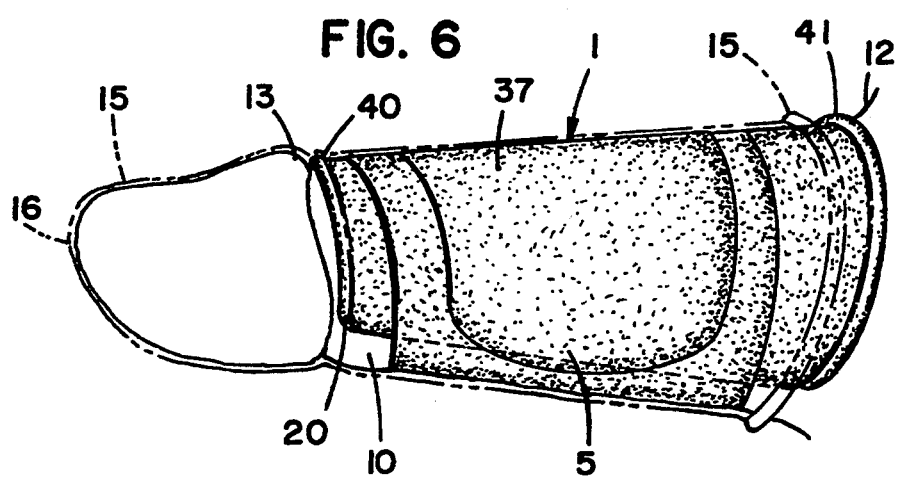

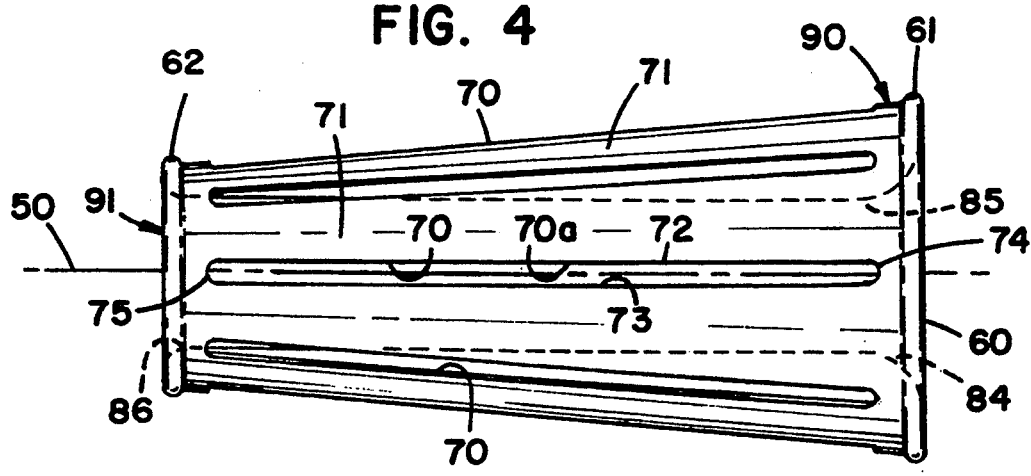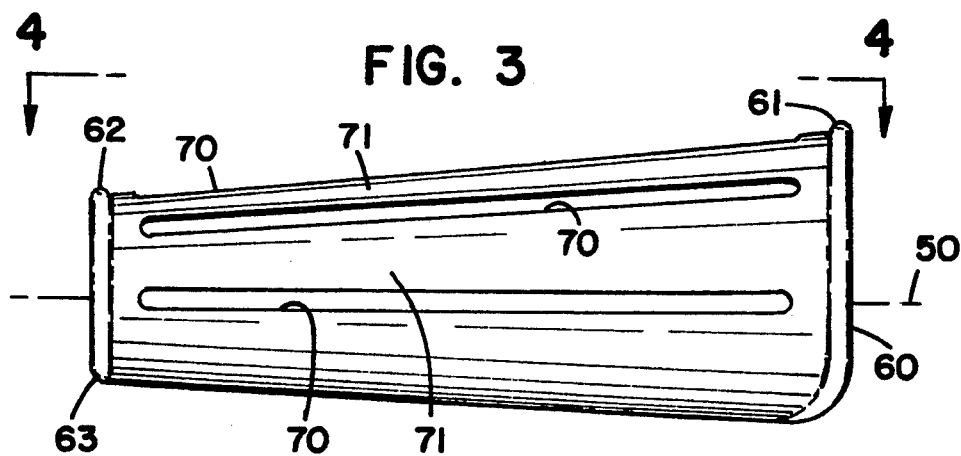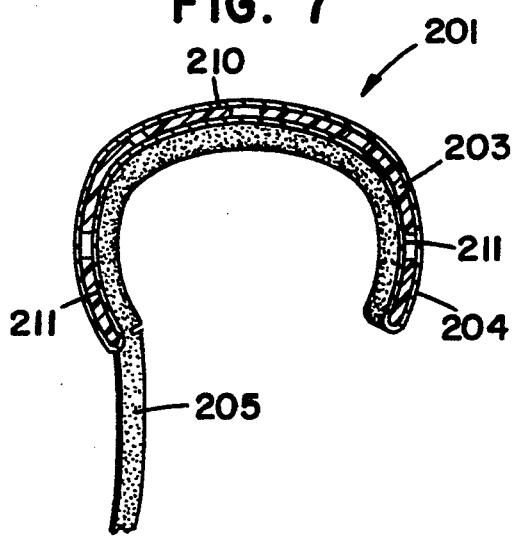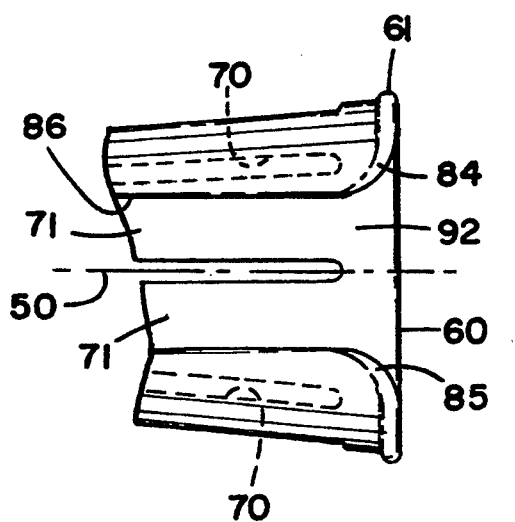

PROSTHETIC DEVICE WITH A RETAINING STRAP

The present application is a File Wrapper continuation of U.S. Ser. No. 07/872,629, filed Apr. 22, 1992, now abandoned. Application Ser. No. 07/872,629 was a continuation-in-part of application Ser. No. 07/600,612, filed Oct. 19, 1990, now abandoned. Application Ser. No. 07/600,612 is incorporated herein by reference.

FIELD OF THE INVENTION

The present invention generally relates to prosthetics and prosthetic devices. More specifically, the invention concerns devices utilizable to support the human penis, during sexual activity.

BACKGROUND OF THE INVENTION

For a variety of reasons, many human males are totally or partially sexually dysfunctional. Causes or factors relating to this dysfunctionality have been widely studied and are under continual examination. In general, a variety of causes and/or factors are known, including both physical (medical) and mental (psychological) ones.

In many instances the dysfunction is only partial. For example, the male may be physically capable of engorging and thus enlarging the penis, but cannot obtain a sufficiently rigid erection for sexual activity, or cannot maintain one for a sufficient period of time to satisfactorily complete intercourse.

A wide variety of devices have been developed to assist the sexually dysfunctional male in maintaining an erection. Some are surgical implants, which when manipulated simulate a rigid erection. Others are external aids which, when applied or mounted, serve to partially simulate an erect penis.

It is the latter type (i.e. external type) of aide which is of particular interest herein. Past such aides have generally been less than completely acceptable for their function, for a variety of reasons. For example, some such aides are not comfortable when worn by a user. Others do not involve a sufficiently secure mounting system for convenient use. Others, while they may be somewhat comfortable when mounted, are not comfortable to one or both parties during the act of intercourse.

Another problem with conventional arrangements is that in general they have not been designed specifically for changes in the diameter and/or length of the penis during the act of intercourse. For example, under the stimulations associated with the sex act, the male partner's sex organ may become further engorged, or less engorged, with passage of time, prior to orgasm. Conventional prosthesis have not, in general, been constructed to comfortably allow for such changes or fluctuations.

Another problem with conventional prosthesis concerns the nature of the prosthesis, and the mental state of the dysfunctional male. Some males find that the inability to maintain sufficient erection for sexual intercourse is in some manner embarrassing. It can at least be speculated that such males would prefer the utilization of prosthesis which may, in at least some instances, be used without the knowledge of their sex partner and which, even if used with the knowledge of the sex partner, in use presents a generally natural appearance and feel. In general, conventionally available prosthesis have not provided for this.

In still other manners conventional prosthesis have not been totally acceptable. The shape of the male sex organ may very from person to person, and many prostheses have not been designed to accommodate this. Some males may be partially or completely circumcised, and many prostheses have not been developed to accommodate, comfortably, the foreskin of a male who is not circumcised or who is partially circumcised.

Still other problems concern birth control and problems with control of sexually transmitted diseases. In many instances it has been desirable for the male to be able to utilize a condom or the like, for birth control and/or disease control. Some conventional prostheses have not readily and conveniently accommodated the utilization of such birth control aides or disease control aides.

In general, what has been needed has been an improvement in the prosthesis art such as to result in the development of a male sex prosthesis which reflects improvement in some or all of the above recited areas. Methods for the utilization of such arrangements, effectively, have also been needed.

SUMMARY OF THE INVENTION

According to one aspect to the present invention there is provided a prosthesis for use by human male in supporting the penis during sexual intercourse. The prosthesis comprises an elongate trough member sized to be fit over the penis of a user at a location behind the glans. One preferred trough member includes a plurality of spaced longitudinal slots therein, to provide for a type of longitudinal flexibility as described herein. The prosthesis includes retaining means for maintaining the trough member in operative association over the user's penis, during performance of intercourse. In one embodiment the retaining means includes a sheath enclosing the trough member, for comfort; and, a tail piece operationally positioned to be wrapped around the trough member and the wearer's penis, during mounting. In another embodiment the retaining means is provided by the preferred size and shape of the trough member, in association with a mounting strap or stirrup.

For preferred embodiments, the trough member has a generally C-shaped cross-section and, when mounted, is oriented with the open portion of the C cross-section directed generally downwardly. That is, in use the device is preferably fit over the *corpora cavernosa* with the open part of the "C" cross-section directed toward the *corpus spongiosum*.

For preferred embodiments, in use the prosthesis is not constant in cross-sectional curvature throughout its longitudinal extension. Rather, the device comprises a longitudinal extension having a first end of a first radius of curvature and a second end of a somewhat larger radius of curvature; the second end being adapted to be positioned against the region of the pubic bone of a wearer, during use. For certain embodiments preferably the inside radius of curvature of the second end is at least about 0.5 inches greater than the inside radius of curvature of the first end, for comfort. Also, in some applications, at the second end the trough member may include outwardly flared corners, to facilitate comfort.

In certain preferred applications, the trough member comprises a polymeric plastic material, preferably selected from the group consisting of polypropylene and polyethylene plastic materials. Such materials can be readily provided in a structure possessing the characteristics described herein. In certain, preferred, alternate embodiments, urethane and latex may be used to advantage. The most preferred embodiments preferably are radially flexible, as described herein below, for comfort.

To facilitate substantial radial-rigidity in those embodiments which are radially rigid, certain embodiments according to the present invention include at least one radial bead therein, for radial strength. Preferably the bead is formed integrally with, or molded into, the trough member, i.e. it preferably comprises a portion or narrow rib of the trough member of a relatively high average thickness. Most preferably, the radial bead is positioned adjacent the second end, i.e. end of larger radius, of the device. In typical, preferred applications, especially wherein the trough member is formed from a polymeric plastic, the trough member will have an average thickness of about 1/16 to ⅛ inches, with the radial bead providing for a total thickness of about ⅛ to ⅜ inches thereat, i.e. the bead being about 1/16 to ¼ inch thick.

In those applications involving slots, the longitudinal slots comprise at least 60%; and more preferably at least 85%, of the length of the prosthesis. Preferably each slot is positioned at least about 0.25 inches, and preferably about 0.37-0.50 inches, from each next adjacent slot.

If sheath material is used, preferably the sheath material is formed from soft smooth polymeric material exhibiting a relatively high coefficient of friction against human skin; and, the tail member is formed from the same material as the sheath. Preferably the tail member is mounted in the device in such a manner as to provide a space or slot between the tail member and the sheath immediately adjacent the trough member first end; the slot defining a retaining flap usable to readily accommodate the foreskin of a wearer, for comfort. Preferably the slot is oriented such that the foreskin of the wearer can be pulled back over the sheath somewhat, to be wrapped underneath the retaining flap during mounting.

To facilitate retention of the trough member in place during use, its inner surface may be pebbled during molding and construction. Pebbling produces a rough inner surface to increase the coefficient of friction thereat. This may be used for all embodiments described herein.

According to the present invention, a method of supporting the penis during sexual intercourse performed by a sexually dysfunctional (partial or total) human male is provided. In certain applications, the method comprises steps of: positioning a trough member over the user's penis with the other part of the "C" shape directed downwardly or away from the belly, the trough member possessing sufficient longitudinal rigidity to support the penis; wrapping a thin flexible tail member around the trough member and the user's penis; and, positioning a condom over the trough member, tail member and penis. In preferred applications of this method, the trough member is as described above. In alternate applications, a sheath member is avoided and a mounting strap or stirrup is provided.

The drawings constitute a portion of the specification and include exemplary embodiments of the present invention. It will be understood that in some instances relative component sizes and material thicknesses may be shown exaggerated, to facilitate an understanding of the invention.

Alternate embodiments of prosthesis according to the present invention are provided which include means for retaining the prosthesis in place through utilization of a retaining strap operably positioned to circumscribe a portion of a body, or an article on a body, of a wearer. Alternate embodiments are shown wherein the retaining strap comprises a thin flexible strap sized and situated to extend around the scrotum of a wearer, or some other portion of a wearer or an object on a wearer. In one alternate embodiment, the retaining strap is directed for engagement with a second strap on the wearer.

In certain preferred applications, the trough member is quite radially flexible, with good memory. Thus, it can be expanded to be placed in position, but will contract for a snug, comfortable, fit. For such an embodiment preferably an FDA approved thermoplastic rubber is used.

BRIEF DESCRIPTION OF THE DRAWINGS

FIG. 1 is a perspective view of a device according to a first embodiment the present invention.

FIG. 2 is a fragmentary cross-sectional view of the device shown in FIG. 1, taken generally along line 2—2 thereof.

FIG. 3 is a side elevation view of a component of the device illustrated in FIG. 1.

FIG. 4 is a top plan view of the component depicted in FIG. 3, taken generally from the point of view of line 4—4 thereof.

FIG. 5 is a fragmentary, bottom plan view of the arrangement shown in FIG. 3.

FIG. 6 is a view of the arrangement shown in FIG. 1, depicted operably mounted for use.

FIG. 7 is a view analogous to FIG. 2, for an alternate embodiment.

DETAILED DESCRIPTION OF THE INVENTION

Figure 8:
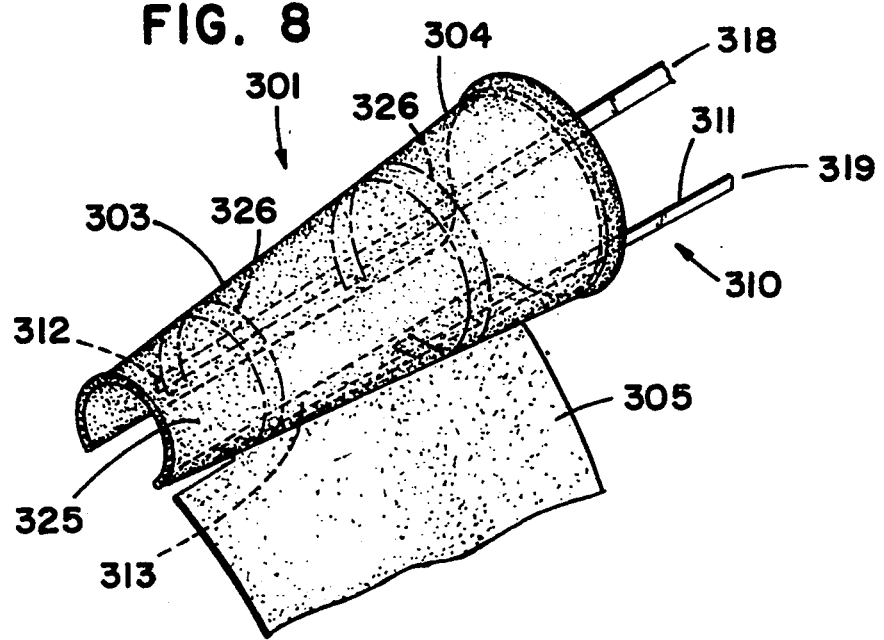
FIG. 8 is a fragmentary perspective view of a device according to a second alternate embodiment of the present invention; the perspective of FIG. 8 being generally analogous to that of FIG. 1.

Herein a detailed description of the present invention is provided. The description is made with reference to accompanying drawings, and specific features of the preferred embodiment depicted therein. It is to be understood that the specific features of the drawings are intended to be exemplary, for a general understanding of the basic principles of the present invention.

Embodiments of FIGS. 1-6

Reference numeral 1, FIG. 1, generally refers to a device according to a first embodiment of the present invention. The device 1 comprises an elongate, generally cylindrical trough member 3 enclosed within a sheath 4. The sheath 4 includes attached thereto, or preferably formed integrally and continuously therewith, an elongate mounting flap or tail 5. As will be apparent from the following, the sheath 4 and tail 5 together comprise retaining means for maintaining the trough member 3 in operative association with a user's penis, during use; i.e. during performance of sexual intercourse.

Before specific details of the construction of device 1 are presented, a brief description of its utilization and operation will be presented. With respect to this, attention is directed to FIGS. 1, 2 and 6. As will be understood by reference to FIG. 2, tail 5 is generally an elongate thin, flexible member.

In use, device 1 is fit over a partially engorged, i.e. a partially enlarged and elongated but insufficiently rigid for sexual activity, penis 10. The device 1 is generally and preferably sized to snugly fit in extension between a region 12 of the pubic bone, to a point behind the glans 13. The device 1 is secured in position by wrapping tail 5 around the penis 10, and the trough member 3 in combination, as shown in FIG. 6. In general, the wrapping would preferably be in the direction indicated by arrow 6, FIG. 2.

It will be preferred that in use a condom 15 be positioned over the mounted device 1. That is, a condom 15 is utilized as a sleeve to maintain comfortable, secure, mounting of the device 1. In some instances a condom allowing for a larger than average diameter male may be preferred for comfort. If it is desired that the condom 15 not interfere with procreation, the end 16 thereof can be punctured or otherwise cut open to allow passage of semen therethrough.

An important feature regarding utilization of the device 1 can be readily understood by reference to FIG. 6. In general, device 1 is preferably mounted over the partially engorged penis 10, rather than under same. That is, trough member 3, preferably generally cylindrical in configuration, includes an open slot 20, FIG. 1, therein, i.e. trough member 3 has an open C-shaped configuration in cross-section. In preferred use, the device 1 is fit over the penis, with slot 20, i.e. the open part of the C-shaped cross-section, directed generally downwardly or away from the belly. Reasons for this will be apparent from further descriptions herein below.

To facilitate mounting in this manner, preferably the "open" portion of the C-shaped cross-section comprises a gap of at least about 0.5 inches across, for the average male, FIG. 6, it is foreseen that a gap of about 0.75 to about 1.5 inches will be preferred. The "gap" in this instance is the distance between opposite edges of the trough member 3, across the open part of the "C". If a circular radius is used for the C-shaped cross-section, typically a gap extending across an arc of 50° to 110° will be preferred, again for the average male.

Specific features regarding the construction of device 1, provide for comfortable and convenient use, both for the user, and for the user's sex partner. Details of preferred construction with respect to each of the trough member 3, sheath 4 and tail 5, are of significance with respect to this.

Referring to FIG. 1, preferably the sheath 4, in which the trough member 3 is enclosed, is provided of a relatively soft, smooth, material which exhibits a relatively high coefficient of friction against human skin. In preferred embodiments, the inner surface of the sheath is pebbled, to facilitate retention in place during use. Herein, the term "relatively high coefficient of friction" in this context is meant to refer to a coefficient sufficiently high so that the device 1, when mounted, is not likely to slide relative to the user's penis, during normal intercourse activity. Thus, at least in part as a result of this relatively high coefficient of friction, device 1 will remain in place, during intercourse. A variety of suitable materials may be utilized with the sheath 4, including latex rubber materials or the like. One such material is the material from which external urinary catheters are formed. It will be readily understood from the previous description of use, that a relatively high degree friction between an outer surface 25 of sheath 4, or outer surface 25a of tail member 5, and the user's sex partner is of little concern, since in preferred use the device 1 will be received beneath a condom 15 or the like, which can provide for comfortable lubricated movement and natural feel. Referring to FIG. 2, the relatively high coefficient of friction to prevent sliding in the area of inner surface 26, however, will again help secure device 1 in place on a wearer, during even during relatively rigorous sexual activity.

The overall thickness of sheath 4 can be varied, as long as it provides for sufficient protection of core 3, and comfort for the user and the user's partner. It is foreseen that if polypropylene or polyethylene is utilized as the trough material underneath a latex sheath material, in general an overall thickness of about 0.1 to 0.3 inches, i.e. thickness from either one of surfaces 25 or 26 through to the trough member 3, FIG. 2 will in general be useable and preferred.

Referring to FIG. 1, tail 5 is shown mounted along sheath 4 at region 30, along substantially an entire longitudinal extension of device 1. Tail 5 may comprise a separate and different material from sheath 4, merely attached to sheath 4 in region 30. In the alternative, and as shown in the preferred embodiment of FIG. 1, tail piece 5 may preferably comprise a thin, flexible extension of same material as sheath 4, molded, extruded or otherwise generated continuously with sheath 4 and region 30, i.e. without a seam (seamless). Thus, for the arrangement shown in FIG. 1, tail 5 preferably comprises a flexible extension of the same latex from which sheath 4 is preferably formed.

Referring to FIG. 1, the tail 5 depicted therein is shown in a preferred configuration having an outer periphery 32 with the generally U shaped configuration, i.e. wide in region 30 and, narrowing to a rounded point at region 35. Thus, when wrapped around sheath 4 and a wearer's penis, FIG. 6, tail 5 will tend to build up in thickness, to a maximum extent, in central portion 37 of the sheath 4. This will prevent a substantial bulge in the material near either of ends 40 and 41 of the sheath. Avoidance of bulges in these regions may be desirable, for both comfort of the wearer and also comfort of the wearer's partner. In general, tail 5 should be long enough to wrap around the arrangement at least about 1.5-2 times. In typical application a length of about 5 to 11 inches will be sufficient.

Referring to end 40, for the preferred embodiment, sheath 5, in region 30, includes a notch or slot 45 thereat creating mounting flap 46. This facilitates comfort of the wearer should the wearer have substantial foreskin immediately behind the glands. Such foreskin, if present, can be pulled backwardly over sheath 4 and then wrapped underneath tail 5; notch 45 and flap 46 accommodating, comfortably, the presence of the foreskin. In the absence of notch 45 and flap 46 such foreskin would tend to be pinched in this location, causing discomfort and possible injury, especially during intercourse. A notch or slot 45 of about 0.5 to 1.5 inches in length (and preferably about 1 inch) will typically be sufficient for achievement of the desired effect.

Many of the advantageous features of device 1, result from the nature and construction of trough member 3. In general, for the preferred embodiment illustrated in FIGS. 1 and 2, trough member 3 is formed from a relatively thick, smooth material. It will be understood that a variety of materials may be utilized. Preferred materials include polyethylene and polypropylene plastics, or similar polymeric plastics.

Preferably the material from which trough member 3 is formed is sufficiently radially-rigid so that it does not tend to compress over the user's penis, causing discomfort or impairing circulation, as tail 5 is wrapped tightly therearound and/or during intercourse. That is, preferably core 3 is constructed in a manner such that it tends to resist harmful "radial" collapse, i.e. an uncomfortable tightening or pinching down toward central longitudinal axis 50 thereof, under the type of pressures that would be associated either with the wrapping of tail 5, or intercourse itself. One manner in which this can be controlled is through utilization of an appropriately strong plastic, of appropriate thickness. The device shown in FIG. 1 includes an end rib or bead 55 which facilitates resistance to radial collapse. Herein this resistance to radial collapse will be generally referred to as "substantial radial-rigidity". This term and variants thereof, is meant to refer to a trough member 3 sufficiently rigid or resistant to radial collapse, so as not to uncomfortably tighten over a user's penis, during intercourse. Bead 55 also facilitates comfort, as it broadens an end of the device whereat it is positioned against a user's pubic area.

Trough member 3 is depicted without sheath 4 and tail 5 thereon, in FIGS. 3, 4 and 5. Referring to FIG. 3, trough member 3 includes an end 60, which generally corresponds to end 41, FIG. 1. End 60 is shown with the molded outer bead 61 thereon, which in cooperation with sheath 4 forms rib 55. For the preferred embodiments shown rib or bead 61 represents a relatively thick, strong, structural component which will facilitate resistance to radial collapse, of trough member 3. This, as explained above, is advantageous. For the arrangement shown in FIG. 3, a second bead 62 positioned at an end 63 opposite to end 60 further facilitates radial strength. The second bead 62 is preferably of about the same thickness as the first bead 61.

In general, it will be desirable that trough member 3 be constructed in a manner allowing for a specific type of longitudinal flexibility, i.e. a type of flexibility along its length of extension. This will facilitate comfort for the wearer, as the extent of penis engorgement fluctuates during sex activity. Further, it will facilitate both the wearer's comfort and the wearer's partner's comfort, during the sex act. One problem with many conventional arrangements is that they are so rigid in extension, they are very uncomfortable for the wearer's partner during normal intercourse, or in various sex positions. Herein, the term "substantial longitudinal flexibility" and variants thereof is meant to refer to this flexibility; i.e. flexibility sufficient for comfort and to allow for fluctuation in penile engorgement while at the same time sufficiently rigid to simulate erection in use. The specific type of flexibility referred to in this context, is one which results from features detailed below.

For the arrangement depicted in FIGS. 1 and 3, substantial longitudinal flexibility is provided at least in part by means of spaced slots 70. Between slots 70 strip 71 will provide for a type of longitudinal flexibility, facilitating comfort. Preferably slots 70 are provided sufficiently wide such that no site of pinching between opposite edges, for example opposite edges 72 and 73 of slot 70a, is likely. Also, preferably ends 74, 75 of the slots 70 are rounded, to inhibit splitting and to facilitate comfort.

For the preferred embodiment illustrated in FIG. 1, preferably the slots are each at least about 1/32 to ⅛ inches wide. Also, preferably each slot extends for at least about 60%, and more preferably at least about 85%, of the overall length of trough member 3, to facilitate the selected type longitudinal flexibility along most of the longitudinal extension of device 1. In general, a preferred spacing between adjacent slots is about 0.5 to 1.5 inches, although a variety of spacings may be utilized. Referring to FIGS. 3 and 4, slots 70 are shown diverging, in extension from ends 75 to end 74, relative to one another. This arrangement results in part through accommodation of tapering described below for the overall longitudinal extension of member 3. It will be understood that in some applications slots 70 may be prepared extending generally parallel to one another, rather than in the diverging pattern illustrated.

For arrangements such as those depicted, preferably the material from which the trough member is formed has a thickness of about 1/6 to ⅛ inches, with each radial bead providing for a total thickness of about ⅛ to ⅜ inches thereat. That is, preferably each radial bead is about 1/16 to ¼ inch thick.

Advantages due to a type of increased flexibility indeed result from a slotted arrangement, as will be apparent from descriptions herein. In particular, strips 71 are independently somewhat flexible, and allow some movement for comfort. The slots, 70 it will be understood, can be provided in member 3 in a variety of manners including by being cut or stamped therein, or by being molded therein during a molding operation.

In preferred applications member 3, and thus device 1 when sheath 4 is provided over member 3, is not perfectly cylindrical, but rather has an advantageous configuration including a first inside or inner radius of curvature at end 60 and a second radius at end 63, the radius at end 60 being larger than the radius at end 63. Also, preferably at end 60 corners 84 and 85 in slot 86 (corresponding to slot 26 when covered by sheath 4, FIG. 1) are flared somewhat, for comfort. Thus, member 3, and resulting device 1, include a relatively large radius flared end 90, sized for comfortable placement against the public bone of the wearer. Opposite end 91, however, preferably has a relatively small radius of curvature in comparison, facilitating secure placement behind the glans of the wearer, FIG. 5. Herein, the term "radius" in this context is meant to refer to the radius of curvature of the inner surface 92 of device 1 or the inner surface 26 of member 3, FIG. 5.

It is noted that the embodiment of FIGS. 1–5, thus far described, is provided with member 3 having a generally circular C-shaped configuration. Alternate embodiments are available, for example wherein a C-shaped curve is provided with a more flattened and oval configuration. Such an embodiment is illustrated in FIG. 7, as discussed below. In general, it is foreseen that for such arrangements dimensions generally similar to those described above will be preferred, except for the slightly flattened configuration to facilitate comfort for some wearers.

In typical applications, for most males, the internal radius of end 90 will preferably be about 0.5 to 1.0 inches larger than the internal radius of end 91. Of course, there is a wide variety of differences in the circumference of the penis, among human males. It is foreseen that depending upon the wearer, the overall internal radius of curvature of end 91 would generally preferably be about 0.5 to about 1.5 inches.

Referring to FIG. 1, the preferred embodiment illustrated a relatively constant increase in the internal radius is shown, along extension from end 40 to end 41. That is, the arrangement illustrated in FIG. 1 represents, substantially, a truncated conical shape. This results, FIG. 3, from relatively constant increase in radius from end 91 to end 90 of member 3, with a relatively constant thickness of sheath 4, FIG. 1.

It will be understood that advantages may be obtained, in the absence of a constant increase in radii of curvature. That is, for some embodiments a relatively constant radius of curvature could be utilized over a portion of the device, with an end flare or widening in the end corresponding to end 41, FIG. 1. The particular choice will depend, in part, upon the amount of flaring over the longitudinal extension device 1, considered to be most comfortable for any particular wearer.

A variety of dimensions may be utilized for devices 1 according to the present invention, due to variations in the human population. In general, the device 1 should be constructed to be of appropriate length to snugly fit between the pubic bone and the glans of the wearer. Since the glans of the wearer generally comprises about 1.0 to 1.5 inches or so in length, typically the overall length of device 1 will be about 1.0 to 1.5 inches less than the overall length of the user's partially engorged penis.

From the above descriptions, a variety of alternative constructions will be readily understood. For example, if constructed from the materials described above, the circumferential rigidity of the device 1 will have generally resulted from the material utilized to create member 3, since sheath 4 would be understood to be generally flexible material such as latex. It will be understood that member 3 could be formed from a relatively flexible material, as long as the material when in combination with sheath 4 is radially rigid. In the alternative, member 3 could be provided from somewhat flexible material formed with ribs utilized in association with stays that would provide for sufficient rigidity and relative flexibility where needed.

Alternate Embodiment of FIG. 7

As referenced above, in some applications it is foreseen that the principles of the present invention may be applied to arrangements not having a circular C-shaped configuration, but nevertheless having a generally C-shaped configuration. Such an embodiment is illustrated in FIG. 7, which comprises a cross-sectional view generally analogous to that of FIG. 2, for such an arrangement. Referring to FIG. 7, a device 201 is depicted comprising an elongate trough member 203 within sheath 204. The sheath includes attached thereto mounting flap or tail 205.

For the arrangement shown in FIG. 7, the trough member 203 includes a central arcuate portion 210, and outer lips or flanges 211. For the arrangement shown in FIG. 7, preferably the internal radius curvature of portion 210 at an end corresponding to end 90 of FIG. 5 would be about 0.5 to 1.0 inches larger than the internal radius of an end corresponding to end 91. Also, preferably the overall internal radius curvature for that portion of region 210 in the vicinity of an end of the device 201 corresponding to end 91 FIG. 5 would have an internal radius of curvature of about 0.5 to about 1.5 inches. Regions 211, on the other hand, may have a slightly tighter radius of curvature to generate the preferred configuration depicted.

Figure 9:
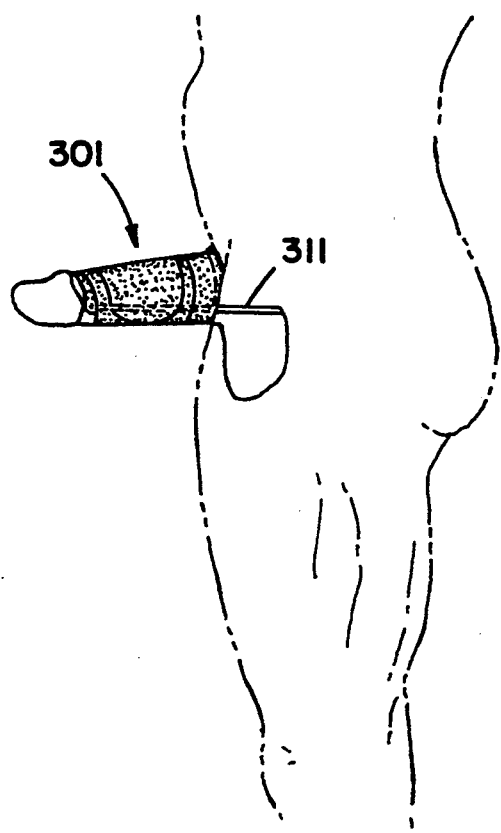
FIG. 9 is a schematic representation of the alternate embodiment of FIG. 8 shown worn by a user.
Figure 10:
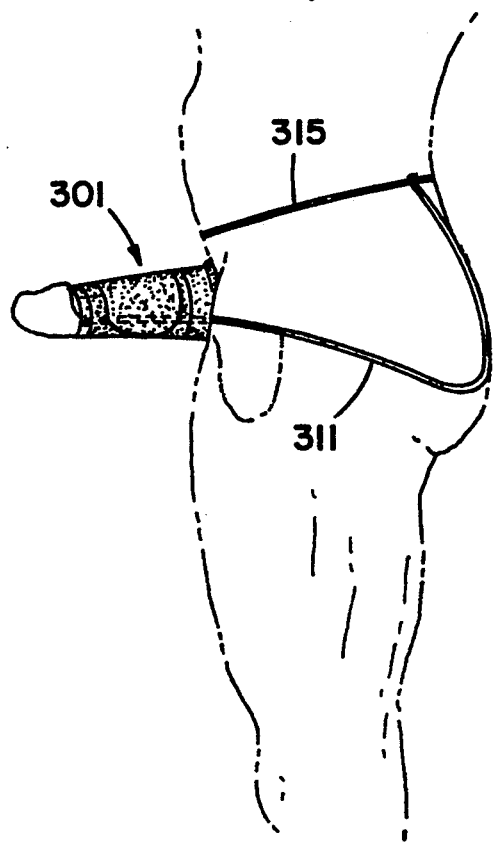
FIG. 10 is a view generally analogous to FIG. 9, of an alternate version of the alternate embodiment of FIG. 8 shown being used by a wearer.

Alternate Embodiments of FIGS. 8-10

It is foreseen that in some applications it may be desirable to provide arrangements according to the present invention with still a further retaining means for selective positioning on a wearer. Attention is directed to FIGS. 8-10, which illustrate such means.

Referring to FIG. 8, but for retaining means described herein below, a device generally analogous to that illustrated in FIG. 1, is shown in a fragmentary perspective view. That is, in FIG. 8 a device 301 is shown comprising an elongate general cylindrical trough member 303 enclosed within a sheath 304 having elongate mounting flap or tail 305. Except as indicated herein below, device 301 may be generally assembled and used similarly to device 1, FIG. 1.

For the arrangement shown in FIG. 8, device 301 includes retaining means 310 in addition to tail 305. The retaining means 310 comprises an elongate strap 311 having first end 312 and second end 313. Strap 311 is shown fragmented at points 318 and 319. In a typical application, strap 311 will be continuous in extension between points 318 and 319, the dimension, i.e. length depending upon the particular embodiment involved.

In use, stirrup or retaining strap 311 will be mounted in association with sheath 304 by being applied to an outer (convex) surface 325 thereof. In particular, ends 312 and 313 are positioned along outer surface 325 of sheath 304. Then, when device 301 is positioned upon a wearer, tail 305 can be wrapped over both sheath 304 and ends 312 and 313 of strap 311, retaining strap 311 in association with sheath 304. If desired, strips of tape 326 or the like may be utilized to facilitate anchoring of strap 311 to sheath 304. It is believed, however, that in preferred applications strips of tape 326 will be avoided, since tail 305 will provide for some adherence. In addition, the strap 311 an be molded to the construction. This is advantageous, since the use of any adhesive in the vaginal area is preferably avoided.

As indicated above, preferably ends 312 and 313 of strap 311 are mounted along an exterior surface 325 of sheath 304. More specifically, they are preferably mounted on the convex side of device 301, i.e. the side of opposite to wearer during use. This will facilitate comfort.

Manners in which retaining strap 311 can be utilized to facilitate operation device 301, will be understood by reference to the schematic FIGS. 9 and 10. In FIG. 9, device 301 is shown with strap 311 sized to be wrapped around the scrotum of a wearer. In FIG. 10, device 301 is shown mounted with strap 311 extending between the legs of a wearer, to the wearers backside, and upwardly into engagement with a waist loop or belt 315.

From examination of FIGS. 8, 9 and 10, advantage to assist in utilizing mounting strap 311 will be understood. In general, the strap 311 will help maintain device 301 in position on a wearer, without slippage.

It is foreseen that a variety of materials and sizes may be utilized for strap 311. In general, the length will depend upon the particular wearer's needs in the portion of the body about which is to be encircled.

It is foreseen that it will be preferable that strap 311 be used under relatively little tension, for comfort of the wearer. The wearer may achieve this desired comfort level, by positioning strap 311 around the appropriate portion of the wearer's body and then laying ends 312 and 313 appropriately along device 301, before wrapping tail 305 thereover.

A variety of materials may be utilized for retaining strap 311. It is foreseen that a particularly useful material will be a thin soft ribbon of rubber latex material, similar to that from which surgical tubing or the device 301 is formed. Again, the length will vary depending upon the particular wearer and proposed use. It is foreseen that a width dimension of about $\frac{1}{8}$ to $\frac{3}{8}''$ will typically be sufficient, if not more than sufficient, for use and comfort. Thickness will depend upon the strength of the material used.

Alternate Embodiments of FIGS. 11-15

Still another alternate embodiment of the invention is illustrated in FIGS. 11-15. The embodiment of FIGS. 11-15 comprises an improved alternate embodiment and is presently believed to be preferred.

Figure 11:
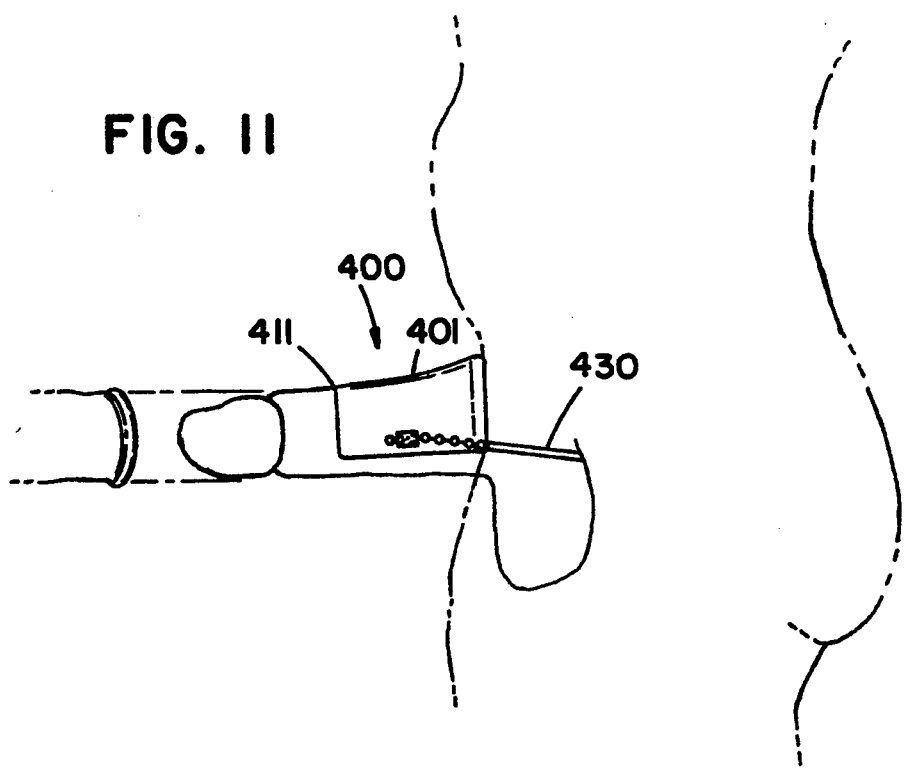
FIG. 11 is a schematic representation of a third alternate embodiment of the present invention shown worn by a user.

Referring to FIG. 11, reference numeral 400 generally designates the preferred device. In FIG. 11 it is illustrated mounted at the pubic bone end of the penis and worn analogously to the device 301, FIG. 9.

Figure 12:
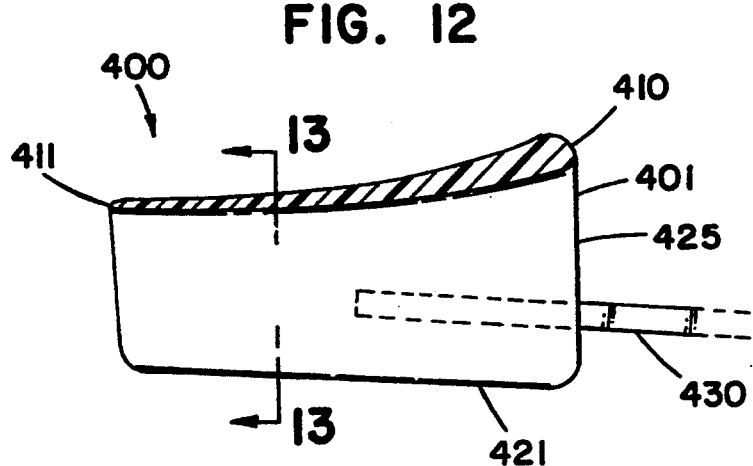
FIG. 12 is a side cross-sectional view of the embodiment of FIG. 11.
Figure 13:
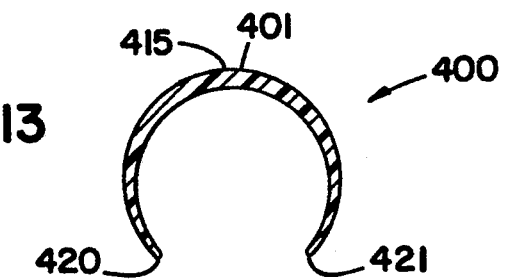
FIG. 13 is a cross-sectional view taken generally from the orientation of line 13—13 of FIG. 12.

Device 400 of FIG. 12 comprises a trough-shaped member 401 having a generally C-shaped cross-section, FIG. 13. (It will be understood that in FIG. 12 the device is illustrated in longitudinal cross-section relative to FIG. 11.)

Arrangement 400 shown in FIGS. 11-15 does not comprise a trough member with slots therein. Rather, device 400 is a molded construction comprising flexible urethane or latex which has selected varying thicknesses throughout to achieve advantage. (Injection molding may be used.) It is not provided with a sheath thereover if constructed of appropriate urethane/latex material. In some instances, however, it may be desirable to provide an outer latex coating of materials such as surgical rubber or the like.

A first, major, manner in which the embodiment of FIGS. 11-15 differs from the embodiments of FIGS. 1-10 is in the nature of radial-rigidity. In general, the embodiment of FIGS. 1-10 was radially rigid; i.e. it did not flex radially but rather retained its defined shape. The embodiment of FIGS. 11-15 distinctly differs from this, to advantage. Preferably the embodiment of FIGS. 11-15 is formed from a flexible high memory material which is somewhat elastic. Thus, it can be stretched open radially, fit over the penis of a wearer and then allowed to collapse and snugly fit around the penis of a wearer. A preferred, comfortable, snug fit can be obtained by shaping the article such that the position of memory or rest is at a radial size that will be comfortable for the intended user. An advantage from allowing for radial flexibility is that the device can be expanded more toward on end than another; i.e. can be expanded more toward the pubic area of the wearer than further along the shaft of the penis.

Preferred materials for construction of the trough member are FDA approved thermoplastic rubbers, such as natural (coverless) Mansanto Santoprene, in U.S.P. class no. 6. This is a pharmaceutical medical material known to be safe when positioned in a body cavity and/or when subjected to body fluids. It can be obtained from Mansanto in a variety of thicknesses, depending upon heat and pressure applied. It can be readily molded into configuration such as those shown in FIGS. 11-14.

Another substantial difference between device 400 and the devices previously described herein concerns certain of its dimensions. Preferably, device 400 is constructed with a longitudinal dimension (length) approximately $\frac{1}{3}$ to $\frac{2}{3}$ (preferably at least $\frac{1}{2}$) of the length of the flaccid or partially engorged penis (i.e. the penis as engorged as the particular individual is able to maintain). For the average male, the length of the partially engorged penis is about 4.0 to 5.0 inches. The preferred average length of device 400, for the average male, will be about 2-3 inches, and preferably about 2.25-2.75 inches. Referring to FIG. 12, the longitudinal dimension represents approximately the length of a straight line drawn between points 410 and 411.

Another important difference between the arrangement of FIGS. 11-15 and the arrangements previously described relate to the shape and thickness of member 401. At point 411, the device 400 is relatively thin, with no bead thereon. Preferably the front 411 comes to a relatively fine but rounded edge. In extension between point 411 and point 410, device 400 gradually increases in thickness up to approximately $\frac{1}{4}$-$\frac{3}{8}$ inches. The thickness increase is most pronounced along central section 415, FIG. 13. The central section 415 is the portion of device 400 centrally spaced between the two edges 420 and 421. In general use, section 415 of device 400 is positioned centrally above the penis of a wearer.

In general, device 400 tapers in thickness between section 415 and each of edges 420 and 421, FIG. 13. The gradual decrease in thickness facilitates comfort.

An additional advantage is provided from the dimensions and shape described hereinabove. The relatively thick central section 415 provides for good longitudinal strength in the root area of the penis of a wearer, facilitating support with comfort. Allowing at least approximately $\frac{1}{3}$ (preferably at least $\frac{1}{2}$) of the penis of the wearer to extend beyond the device 400, however, permits flexibility for comfort of the wearer and the wearer's sex partner. In addition, under such circumstances device 400 will not penetrate very far into the female, during intercourse. The tapering to the relatively thin edges along tip 411 and edges 420 and 421 facilitates comfort for the wearer and the wearer's sex partner. Relatively thick dimension along point 410, and in general along back wall 425, FIG. 12, facilitates positioning device 400 against the pubic area or bone of a wearer with comfort.

In preferred embodiments, the inner surface of device 400 is provided with pebbling, to increase its coefficient of friction against skin. This will help retain the device 400 in place, during use.

Unlike with certain previous embodiments, the embodiment of FIGS. 11-15 does not involve mounting with a wrap-around tongue or sheath. Rather, preferably the arrangement of FIGS. 11-15 is mounted with a stirrup or strap 430. The strap 430 is connected at opposite ends to the trough member 401. The strap 430 is sized to extend around a portion of the body of a wearer. It may extend, for example, around the scrotum of a wearer similarly to the strap illustrated in FIG. 9. In the alternative, it may be mounted similarly to the strap illustrated in FIG. 10.

Figure 14:
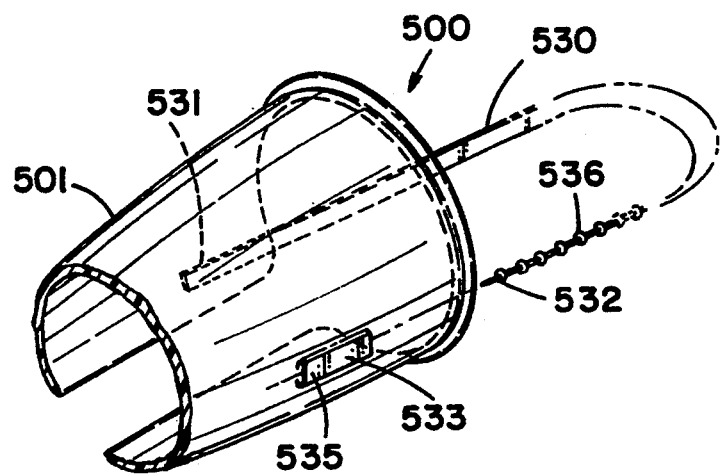
FIG. 14 is a fragmentary perspective view of the arrangement shown in FIGS. 11-13, with a first means of mounting an engagement strap depicted.
Figure 15:
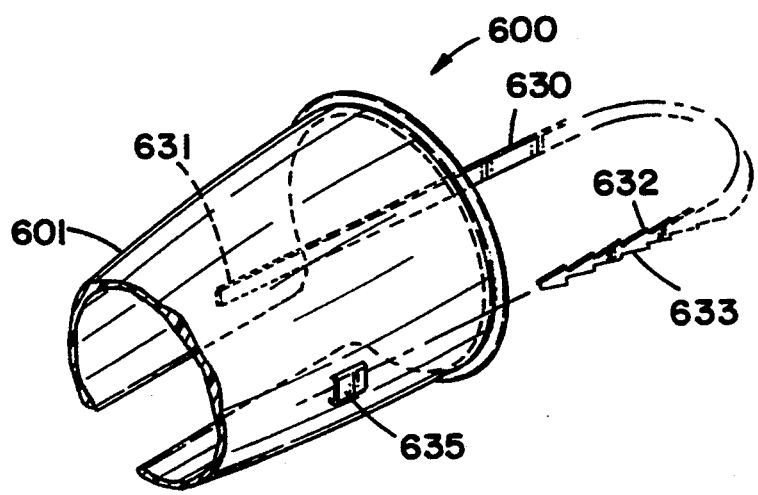
FIG. 15 is a fragmentary perspective view generally analogous to FIG. 14, with an alternate means of mounting an engagement strap illustrated.

Attention is directed to FIGS. 14 and 15 with respect to alternate methods of mounting the strap 430. In the arrangement 500 illustrated in FIG. 14, the strap 530 is connected at one end 531 by molding or similar means. The opposite end 532 of the strap 530 includes means thereon for engagement with connector means 533 on the trough member 501. In the arrangement of FIG. 14, connection is facilitated by a low-profile slot arrangement 535 engageable by a ball and link type fastener 536. It will be understood that the user would extend end 536 into the slot of connector 535, adjusting the amount of extension into the slot for comfort. The excess portion of end 532 can be torn or cut off and discarded. When the device 500 is to be removed, a remaining link can be premolded to break, preventing reuse.

The arrangement 600 in FIG. 15 illustrates an alternate mounting system for strap 630. Strap 630 is connected at end 631 to trough member 601. The connection, again, may be by molding or similar means. At end 632 strap 630 includes "ratchet" or "directional tooth" fastener 633, receivable within connector 635. The user may adjust the length of strap 630 by the extent to which end 632 is threaded through a receiving slot in connector 635. The excess portion of the connector on end 632 can be torn or cut off and discarded. The portion of strap 630 having tooth fastener 633 thereon can be readily torn, for removal of the device 600 from a user.

It will be understood that the arrangements of FIGS. 14 and 15 are exemplary only, and a variety of attachment means may be utilized. For example, for the arrangements shown in FIGS. 11-15, both ends of the straps are shown mounted on the exterior surface of trough member 401, alternate attachments (involving an interior surface) may be utilized in some instances. Also, the straps may have connection means at both ends.

As with previously described embodiments, preferably for the embodiment of FIGS. 11-15 the "gap" in the C cross-section (distance between edges 420 and 421) when the device is worn is at least about 0.5 inches, and for the average male about 0.75-1.5 inches. For embodiments having a circular cross-section, a radial gap of 50° to 110° is generally preferred. It will be understood that these dimensions will not necessarily be maintained by the device when it is not worn, since it is radially flexible and may curl to a smaller diameter or radial dimension. If of an appropriately soft, memory material, however, it can be easily expanded and snugly fit on a user.

It is foreseen that preferred arrangements according to FIGS. 11-15 will be manufactured as "single use" devices. That is, they will be used once and discarded. It is an advantage of the embodiment depicted in FIGS. 11-15 that it can be inexpensively manufactured, thus facilitating single use.

What is claimed is:

1. A method of preparing a human male for sexual activity, the human male having a flaccid penis; said method comprising the steps of:
    (a) fitting over a user's flaccid penis a prosthesis comprising:
        (i) an elongate, flexible, rubber-like trough member having a C-shaped cross-section and consisting essentially of a flexible, polymeric, high-memory material; the trough member having a longitudinal dimension of no more than 3.0 inches and being of a longitudinal dimension not greater than about ⅔ of a length of the flaccid penis of a user; the longitudinal dimension of the trough member being such that it does not extend against a glans of the penis, when the trough member is positioned on the penis and against a pubic area of the user; said C-shaped trough member being configured to be operationally positioned over the penis and to have a gap therein of at least 0.75 inches between side edges thereof, when operationally positioned over the penis; the trough member having a front end and a rear end, the rear end having a C-shaped edge and being constructed and arranged to be operationally oriented with the C-shaped edge of the rear end oriented proximate the pubic area of the male user; the trough member front end having a C-shaped edge; and, the trough member having a central longitudinal section extending continuously therealong from said C-shaped edge of said front end to said C-shaped edge of said rear end; the central longitudinal section generally increasing in thickness from the trough member front end to the trough member rear end; and,
        (ii) retaining means for maintaining the trough member in operative association over the user's penis, during performance of sexual activity; the retaining means comprising a retaining strap having first and second ends operably attached to the trough member; the retaining strap being sized to extend around a scrotum of the male user;
    (b) said step of fitting the user's flaccid penis with the prosthesis including:
        (i) positioning the prosthesis over the penis on a side thereof toward the user's belly and with the gap in the C-shaped cross-section directed away from the user's belly;
        (ii) positioning the retaining strap around the user's scrotum; and,
        (iii) positioning the rear end of the prosthesis proximate the pubic area of the male user.

2. A prosthesis for use by a human male in supporting his flaccid penis, during sexual activity; said prosthesis comprising:
    (a) an elongate, flexible, rubber-like trough member having a C-shaped cross-section and consisting essentially of a flexible, polymeric, high-memory material;
        (i) the trough member having a longitudinal dimension of no more than 3.0 inches and being of a longitudinal dimension not greater than about ⅔ of a length of the partially engorged, flaccid, penis of a user; the longitudinal dimension of the trough member being such that it does not extend against a glans of the penis, when the trough member is positioned on the penis and against a pubic area of the user;
        (ii) said C-shaped trough member being configured to be operationally positioned over the penis and to have a gap therein of at least 0.75 inches between side edges thereof, when operationally positioned over the penis; said trough member being constructed and arranged so that, in use, the gap in the trough member extends continuously along a side of a user's penis away from the user's belly;

(iii) said trough member having a front end and a rear end, the rear end having a C-shaped edge and being constructed and arranged to be operationally oriented with the C-shaped edge of the rear end oriented proximate the pubic area of the male user; the trough member front end having a C-shaped edge; and, the trough having a central longitudinal section extending continuously therealong from said C-shaped edge of said front end to said C-shaped edge of said rear end; the central longitudinal section generally increasing in thickness from the trough member front end to the trough member rear end; and, (b) retaining means for maintaining the trough member in operative association over the user's penis, during performance of sexual activity, the retaining means comprising a retaining strap having first and second ends operably attached to the trough member; the retaining strap being sized to extend around a scrotum of the male user.

* * * * *